(12) United States Patent
Kraling et al.

(10) Patent No.: US 10,966,920 B2
(45) Date of Patent: Apr. 6, 2021

(54) EFFERVESCENT TABLETS THAT INCLUDE CRYSTALLINE SUGAR BINDER AND METHODS OF MAKING THE SAME

(71) Applicant: Amerilab Technologies, Inc., Plymouth, MN (US)

(72) Inventors: Carrie Kraling, Minneapolis, MN (US); Sarah Olson, Minneapolis, MN (US); Shayna Jilek, Woodbury, MN (US)

(73) Assignee: Amerilab Technologies, Inc., Plymouth, MN (US)

( * ) Notice: Subject to any disclaimer, the term of this patent is extended or adjusted under 35 U.S.C. 154(b) by 0 days.

(21) Appl. No.: 16/374,560

(22) Filed: Apr. 3, 2019

(65) Prior Publication Data

US 2020/0170935 A1 Jun. 4, 2020

Related U.S. Application Data

(60) Provisional application No. 62/774,112, filed on Nov. 30, 2018.

(51) Int. Cl.

| | |
|---|---|
| *A61K 9/46* | (2006.01) |
| *A61K 9/00* | (2006.01) |
| *A61K 9/20* | (2006.01) |
| *A61K 9/16* | (2006.01) |
| *C13B 50/00* | (2011.01) |
| *C13B 50/02* | (2011.01) |

(52) U.S. Cl.
CPC .......... *A61K 9/0007* (2013.01); *A61K 9/0056* (2013.01); *A61K 9/0095* (2013.01); *A61K 9/1623* (2013.01); *A61K 9/1664* (2013.01); *A61K 9/205* (2013.01); *A61K 9/2018* (2013.01); *A61K 9/2068* (2013.01); *C13B 50/002* (2013.01); *C13B 50/02* (2013.01)

(58) Field of Classification Search
None
See application file for complete search history.

(56) References Cited

U.S. PATENT DOCUMENTS

| | | | |
|---|---|---|---|
| 3,642,535 A | 2/1972 | Graham et al. | |
| 4,013,775 A | 3/1977 | Nelson et al. | |
| 4,059,460 A | 11/1977 | Schollmeier et al. | |
| 4,297,146 A | 10/1981 | Mise et al. | |
| 5,037,657 A * | 8/1991 | Jones | A61K 9/0007 424/466 |
| 6,527,868 B2 | 3/2003 | Moraly et al. | |
| 8,865,948 B2 | 10/2014 | Duflot | |
| 2011/0281008 A1* | 11/2011 | Gootenilleke | A61K 9/0007 426/548 |
| 2012/0058236 A1 | 3/2012 | Fosdick et al. | |
| 2012/0315333 A1* | 12/2012 | Zhou | A61K 9/209 424/484 |
| 2013/0309389 A1 | 11/2013 | Carlson et al. | |
| 2014/0037814 A1 | 2/2014 | Quinlan et al. | |
| 2017/0283335 A1* | 10/2017 | Rainey | C05D 3/02 |

FOREIGN PATENT DOCUMENTS

| | | |
|---|---|---|
| CN | 103098926 | 5/2013 |
| WO | WO2005072759 | 8/2005 |
| WO | WO2010057372 | 5/2010 |
| WO | WO2011-058336 | 5/2011 |
| WO | WO2011130440 A1 | 10/2011 |
| WO | WO2014018569 | 1/2014 |

OTHER PUBLICATIONS

Ribus (2nd Generation Clean Label Lubricant, Oct. 5, 2016, available at https://web.archive.org/web/20161005102755/https://www.ribus.com/nu-mag/, accessed Jul. 16, 2020).*

ADM Corn Processing, Typical Data Information forClintose® Dextrose A, Product Code 015810, available at https://download.siliconexpert.com/pdfs/2013/8/12/1/19/28/622/arches_/manual/pdf.aspxtechdocid7301srce.aspxtechdocid7301srce.pdf? , accessed on Jul. 17, 2020.*

Merriam-Webster "Crystalline" available at https://www.merriam-webster.com/dictionary/crystalline, and "Crystal" available at https://www.merriam-webster.com/dictionary/crystal, accessed on Jul. 17, 2020.*

Daucian, "Utilization of Gum Arabic for Industries and Huan Health," *Am. J. of Applied Sciences*, vol. 10, No. 10, Oct. 1, 2013, pp. 1270-1279.

* cited by examiner

*Primary Examiner* — H. Sarah Park
(74) *Attorney, Agent, or Firm* — Allison Johnson P.A

(57) ABSTRACT

An effervescent tablet that exhibits rapid disintegration is disclosed. The effervescent tablet includes an effervescent agent that includes an acid and a base, a crystalline sugar binder selected from the group consisting of crystalline dextrose, crystalline sucrose, crystalline fructose, and combinations thereof, the crystalline sugar binder being essentially free of excipients, a sweetener that includes at least one of Stevia and Monk fruit, a flavor agent that includes a gum Arabic carrier, and optionally a lubricant derived from rice hulls (e.g., a multi-component integral lubricant).

16 Claims, No Drawings

EFFERVESCENT TABLETS THAT INCLUDE CRYSTALLINE SUGAR BINDER AND METHODS OF MAKING THE SAME

BACKGROUND

The invention is directed to decreasing the disintegration time of tableted effervescent compositions.

Formulating a commercially viable effervescent tablet is more art than science.

Whether components can be formulated into an effervescent tablet that disintegrates in water in a relatively short period of time and exhibits sufficient integrity as a tablet that it can be manufactured, packaged and shipped without falling apart or exhibiting die wall etching, capping, lamination or picking is often unpredictable. The components of an effervescent composition impact the ability of the composition to form a tablet, tablet hardness, tablet disintegration time in water, and the clarity of the resulting solution once the tablet has disintegrated. The components of an effervescent composition also impact the taste of a beverage made therefrom, which is relevant to the consumer when the effervescent composition is intended to be used to form a beverage.

A common ingredient in effervescent tablets is a binder. A variety of binders have been used in tableted effervescent compositions including compressible sugar alcohols (e.g., sorbitol), compressible dextrose, and compressible sucrose. Compressible sugars are prepared in a variety of ways including co-crystallizing and co-precipitating sugar with an excipient such as maltodextrin, maltose, maltriose, starch, starch hydrolysates, gelatin, polysaccharides, corn syrup, and combinations thereof.

Many effervescent tablet compositions also include a sweetener. Recently consumers have had a preference for the sweetener Stevia due to the fact that it is found in nature, is derived from natural origins, and is low in calories. Effervescent tablets formulated with Stevia exhibit a significant increase in disintegration time relative to tablets formulated with artificial low-calorie sweeteners such as sucralose or acesulfame potassium. It is difficult to formulate an effervescent tablet that includes Stevia and disintegrates rapidly.

Some effervescent tablets also include a lubricant. However, effervescent compositions are inherently difficult to lubricate due to the nature of the raw materials used in the formulations and the desire to achieve a tablet that disintegrates rapidly in water and forms a clear solution. In order for many substances to be effective as a lubricant, they must be present in the tablet in very high concentrations. These high concentrations cause the lubricant to significantly inhibit the tablet's ability to disintegrate. In addition, many lubricants are not water soluble. Magnesium stearate, for example, is not water soluble, can impede disintegration in water, and can produce a cloudy aqueous liquid.

There is a need for improving the disintegration time of effervescent tablets that include natural sweeteners. There is also a need to formulate effervescent tablets with natural ingredients and for improving the disintegration time of effervescent tablets formulated with natural ingredients.

SUMMARY

In one aspect, the invention features an effervescent tablet that includes an effervescent agent that includes an acid and a base, a sweetener that includes Stevia, Monk fruit, or a combination thereof, a crystalline sugar binder selected from the group consisting of crystalline dextrose, crystalline sucrose, crystalline fructose, and combinations thereof, the crystalline sugar binder being essentially free of excipients, and a flavor agent that includes gum Arabic. In one embodiment, the tablet further includes a lubricant derived from rice hulls. In another embodiment, the tablet further includes a multi-component integral lubricant derived from rice extract, rice hulls, gum Arabic, and sunflower oil. In another embodiment, the tablet further includes a multi-component integral lubricant that includes rice hull particles, gum Arabic, sunflower oil and at least one extract of rice. In some embodiment, the tablet further includes from 0.8% by weight to 4% by weight of a lubricant derived from rice hulls. In other embodiments, the tablet further includes from 0.8% by weight to 1.5% by weight of a lubricant derived from rice hulls.

In another aspect, the invention features an effervescent tablet that includes an effervescent agent including an acid and a base, a sweetener including Stevia, Monk fruit, or a combination thereof, a crystalline sugar binder selected from the group consisting of crystalline dextrose, crystalline sucrose, crystalline fructose, and combinations thereof, the crystalline sugar binder being essentially free of excipients, and a flavor agent including gum Arabic, the effervescent tablet having a weight of at least 4 grams and a hardness of at least 5 kiloponds, and exhibiting a disintegration time of no greater than 4 minutes and 20 seconds when tested according to the Disintegration Time Test Method.

In one embodiment, the crystalline sugar binder includes crystalline dextrose monohydrate. In another embodiment, the crystalline sugar binder includes crystalline dextrose monohydrate and crystalline fructose.

In some embodiments, the effervescent tablet disintegrates in 25° C. water in no greater than 3.5 minutes.

In another embodiment, the effervescent tablet includes at least 20% by weight of the effervescent agent, and from 20% by weight to 55% by weight of the crystalline sugar binder. In one embodiment, effervescent tablet of claim includes at least 20% by weight of the effervescent agent and from 20% by weight to 55% by weight of the crystalline sugar binder and disintegrates in 25° C. water in no greater than 3.5 minutes. In other embodiments, the effervescent tablet includes at least 20% by weight of the effervescent agent, from 20% by weight to 55% by weight of the crystalline sugar binder, and from 0.4% by weight to 2% by weight of the sweetener. In some embodiments, the effervescent tablet includes at least 20% by weight of the effervescent agent and from 20% by weight to 55% by weight crystalline dextrose monohydrate. In other embodiments, the effervescent tablet includes at least 20% by weight of the effervescent agent, from 20% by weight to 55% by weight crystalline dextrose monohydrate, and from 0.4% by weight to 2% by weight of the sweetener.

In some embodiments, effervescent tablet further includes oil. In one embodiment the effervescent tablet further includes avocado oil. In other embodiments, the effervescent tablet further includes at least 0.50% by weight oil.

In another embodiment, the effervescent tablet has a hardness of at least 6 kiloponds. In other embodiments, the effervescent tablet has a hardness of at least 7 kiloponds.

In some embodiments, the effervescent tablet includes at least 1.5% by weight of a flavor agent that includes gum Arabic. In other embodiments, the effervescent tablet includes at least 2% by weight of a flavor agent that includes gum Arabic. In other embodiments, the tablet is free of flavor agents that are free of gum Arabic (i.e., are free of flavor agents that do not include gum Arabic).

In one embodiment, the effervescent tablet further includes a lubricant derived from rice hulls. In other embodiments, the effervescent tablet further includes a multi-component integral lubricant that includes rice hull particles, gum Arabic, sunflower oil, and at least one extract of rice. In some embodiment, the tablet further includes from 0.8% by weight to 4% by weight of a lubricant derived from rice hulls. In other embodiments, the tablet further includes from 0.8% by weight to 1.5% by weight of a lubricant derived from rice hulls.

In another aspect, the invention features a method of making an effervescent tablet, the method including forming an effervescent composition by combining ingredients with mixing, the ingredients including an effervescent agent including an acid and a base, a sweetener including Stevia, Monk fruit, or a combination thereof, a crystalline sugar binder selected from the group consisting of crystalline dextrose, crystalline sucrose, crystalline fructose, and combinations thereof, the crystalline sugar binder being essentially free of excipients, and a flavor agent that includes gum Arabic, and tableting the effervescent composition on a tableting press to form an effervescent tablet that has a mass of at least 4 grams and a hardness of at least 5 kiloponds and that disintegrates in 25° C. water in less than 5 minutes. In one embodiment, the crystalline sugar binder includes at least 6% moisture. In another embodiment, the crystalline sugar binder is free of excipients. In other embodiments, the crystalline sugar binder exhibits an average particle size of from 140 µm to 440 µm. In one embodiment, the effervescent tablet has a hardness of at least 6 kp.

In some embodiments, the crystalline sugar binder includes crystalline dextrose monohydrate. In another embodiment, the crystalline sugar binder includes crystalline dextrose and crystalline fructose. In other embodiments, the crystalline sugar binder includes crystalline dextrose monohydrate and crystalline fructose.

In other embodiments, the ingredients further include a lubricant derived from rice hulls. In one embodiment, the lubricant is a multi-component integral lubricant that includes rice hull particles, gum Arabic, sunflower oil, and at least one extract of rice.

In other aspects, the invention features an effervescent tablet that includes an effervescent agent including an acid and a base, a sweetener including Stevia, Monk fruit, or a combination thereof, a first binder, a flavor agent including gum Arabic, and a multi-component integral lubricant derived from rice extract, rice hulls, gum Arabic, and sunflower oil, the effervescent tablet having a weight of at least 4 grams and a hardness of at least 5 kiloponds and exhibiting a disintegration time of no greater than 4 minutes and 20 seconds when tested according to the Disintegration Time Test Method.

The invention features an effervescent composition that exhibits good tableting properties and, when formed into an effervescent tablet, disintegrates rapidly in water.

The invention also features an effervescent tablet that includes natural ingredients, such as a natural sweetener, and disintegrates rapidly in water.

Other features and advantages will be apparent from the following description of the preferred embodiments and from the claims.

Glossary

In reference to the invention, these terms have the meanings set forth below:

The term "multi-component integral lubricant" means a lubricant that includes at least two components intimately associated with one another such that they form a single substance.

The term "crystalline" means in the form of crystals that include flat faces (i.e., facets) and sharp angles.

The term "sugar" means a sugar that is a monosaccharide or a disaccharide.

The term "essentially free of" means no greater than 0.3% by weight based on the total weight of solids.

The term "excipient" means an ingredient other than a crystalline monosaccharide or a crystalline disaccharide.

The term "Stevia" means a sweetener derived from the plant species Stevia rebaudiana.

The term "Monk Fruit" means a sweetener derived from the fruit of the plant species Siraitia grosvenorii.

The term "botanical oil" means an oil derived from a part of a plant.

DETAILED DESCRIPTION

The method of making an effervescent tablet includes combining an effervescent agent, a crystalline sugar binder, a natural sweetener such as Stevia or Monk fruit, and a flavor agent that includes a gum Arabic carrier to form an effervescent composition, and tableting the effervescent composition. The resulting effervescent composition can be tableted to a hardness of at least 3 kiloponds (Kp), at least 4 Kp, at least 5 Kp, at least 6 Kp, at least 7 Kp, or even at least 8 Kp and the resulting tablets can disintegrate in water having a temperature of 72° F. (degrees Fahrenheit) (about 25° C. (degrees Celsius)) in less than 6 minutes, less than 5 minutes, less than 5 minutes 18 seconds, less than 4 minutes 20 seconds, less than 4 minutes 10 seconds, less than 4 minutes, less than 220 seconds, less than 200 seconds, less than 180 seconds, no greater than 150 seconds or even no greater than 120 seconds.

The crystalline sugar binder is at least 95%, at least 96%, at least 97%, at least 98%, at least 99%, at least 99.5%, at least 99.7%, at least 99.8%, at least 99.9%, or even 100% pure crystalline sugar on a dry weight basis (dwb) based on the total weight of the solids in the crystalline sugar binder as supplied by the manufacturer. The crystalline sugar binder preferably is essentially free of, or even free of excipients including such excipients as maltodextrin, maltose, maltriose, starch, invert sugar, corn syrup, a starch hydrolysate, and microcrystalline cellulose. The crystalline sugar binder also is essentially free of, or even free of, co-crystallized excipients, coprecipitated excipients, and co-granulated excipients prior to its addition to the effervescent composition.

Suitable crystalline sugar binders include monosaccharides, disaccharides, and mixtures thereof including, e.g., crystalline dextrose (e.g., dextrose monohydrate, and monohydrate α-dextrose), crystalline fructose, crystalline sucrose, and combinations thereof.

Useful crystalline sugar binders optionally include moisture and preferably include no greater than 11% by weight, no greater than 10% by weight, no greater than 9.5% by weight, from 0% by weight to 9.5% by weight, from 6.5% by weight to 9% by weight, or even from 7.5% by weight to 9% by weight moisture.

The crystalline sugar binder preferably is a free-flowing powder of unagglomerated sugar crystals. Useful crystalline sugar binders exhibit an average particle size of from 140 microns (µm) to 440 µm, from 200 µm to 400 µm, or even from 200 µm to 300 µm.

Useful commercially available crystalline sugar binders include, e.g., organic crystalline sugar binders available from Ciranda, Inc. (Hudson, Wis.) including, e.g., ORGANIC CRYSTAL DEXTROGRAPE crystallized dextrose derived from organic grapes, ORGANIC CRYSTAL FRUCTOGRAPE crystallized fructose derived from organic grapes, and ORGANIC CRYSTAL SWEETGRAPE a mixture of crystallized fructose and crystallized dextrose derived from organic grapes, crystalline sugars available from Batory Foods including Velvet Baker's Special Cane Sugar (Chicago, Ill.), crystalline sucrose available from Domino Foods, Inc., (Baltimore, Md.), crystalline dextrose monohydrate available from Meelunie B.V. (The Netherlands), and ADM crystalline dextrose and crystalline sucrose available from Archer Daniels Midland Company (Chicago, Ill.).

The effervescent composition preferably includes at least 20% by weight, at least 22% by weight, no greater than 55% by weight, no greater than 50% by weight, from 20% by weight to 50% by weight, from 22% by weight to 47% by weight, or even from 25% by weight to 35% by weight crystalline sugar binder.

For ease of discussion, throughout this specification the % by weight values provided for each ingredient present in the effervescent composition are provided with respect to the effervescent composition; it is to be understood these same values are also suitable for the effervescent tablet.

The effervescent agent of the effervescent composition includes an acid and a base. The effervescent agent is activated when contacted with an aqueous liquid, e.g., when the effervescent agent is placed in a glass of water. The water liberates the acid and base and enables the acid and base to react with each other to produce a gas (e.g., carbon dioxide). The effervescent composition preferably includes at least 30% by weight, at least 35% by weight, at least 40% by weight, from 35% by weight to 75% by weight, or even from 40% by weight to 70% by weight effervescent agent.

Acids suitable for use in the effervescent agent include, e.g., citric acid, aspartic acid, malic acid, adipic acid, tartaric acid, fumaric acid, succinic acid, sodium acid pyrophosphate, lactic acid, hexamic acid, amino acid hydrochlorides, and acid salts and acid anhydrides thereof, and mixtures thereof. Preferably the effervescent tablet includes at least 10% by weight, at least 15% by weight, at least 20% by weight, from 20% by weight to 50% by weight, from 20% by weight to 45% by weight, or even from 25% by weight to 45% by weight acid.

The base of the effervescent agent preferably is capable of generating a gas such as carbon dioxide in the presence of an acid source and water. Examples of suitable bases include potassium bicarbonate, sodium bicarbonate, sodium carbonate, sodium sesquicarbonate, potassium carbonate, calcium carbonate, magnesium carbonate, zinc carbonate, and mixtures thereof. Particularly useful bases include potassium carbonates, sodium carbonates, and bicarbonates thereof, and combinations thereof. The effervescent composition includes at least 10% by weight, at least 12% by weight, at least 15% by weight, from 10% by weight to 35% by weight, from 12% by weight to 30% by weight, or even from 15% by weight to 30% by weight base.

The effervescent composition includes at least one natural sweetener such as Stevia or Monk fruit. As used herein a "sweetener" is a compound other than the crystalline sugar binders set forth above. Useful sweeteners include, e.g., natural sweeteners (e.g., Stevia, Monk fruit, and combinations thereof), invert sugar, ribose, isomalt, tagatose, sucralose, and mixtures thereof, saccharin and its various salts (e.g., sodium and calcium salt of saccharin), cyclamic acid and its various salts, acesulfame potassium, dihydrochalcone, glycyrrhizin, and sugar alcohols including, e.g., erythritol, xylitol, sorbitol, sorbitol syrup, lactitol, maltitol, and mannitol, and combinations thereof. When present, the effervescent composition preferably includes at least 0.8% by weight, at least 1% by weight, at least 2% by weight, at least 4% by weight, less than 10% by weight, less than 8% by weight, less than 5% by weight, from 1% by weight to 10% by weight, from 2% by weight to 8% by weight, or even from 3% by weight to 5% by weight sweetener.

The effervescent composition preferably includes from 0% by weight to 2% by weight, 0.1% by weight to 2% by weight, from 0.1% by weight to 1.5% by weight, or even from 0.2% by weight to 1% by weight of a natural sweetener such as Stevia, Monk fruit, or a combination thereof.

The effervescent composition also includes a flavor agent that includes a flavor integrally associated with a gum Arabic carrier (gum Arabic is also known as Acacia gum). The term "integrally associated with" means that the flavor and the carrier are intimately associated with one another such that they form a single substance. Useful flavor agents exist in a variety of forms including, e.g., solids (e.g., powders, granulations, spherical and non-spherical particles, nano-particles, and combinations thereof), liquids (e.g., oils), pastes, and combinations thereof. The flavor agent can be used to impart any desired flavor to the effervescent composition including, e.g., lemon (e.g., lemonade), lime, orange, mango-orange, citrus orange, grape, tropical punch, citrus lime, citrus fruit, grapefruit, apple, pear, peach, grape, strawberry, raspberry, cherry, plum, pineapple, apricot, guava, mango, papaya, watermelon, musk melon, pineapple, grapefruit, blueberry, pomegranate, blackberry, tri-berry, ginger, tangerine, cantaloupe, tea, mint, cocoa, vanilla, almond, coffee, and combinations thereof (e.g., multiple berry flavors, watermelon-lemonade, strawberry-lemonade, lemon-lime, cherry-limeade, and combinations thereof).

Useful flavors include natural and artificial (i.e., synthetic) flavors including, e.g., oil-based flavors (e.g., flavors based on natural oils, synthetic oils, and combinations thereof), aromatics, oleoresins, fatty acids, small molecules, alcohols, aldehydes, ketones, esters (e.g., alkadienyl esters, alkyl esters, and alkenyl esters), ethers, acetals, ketals, nitriles, aliphatic carbocyclic compounds, heterocyclic compounds, extracts derived from plants, leaves, flowers, fruits, and stems, organic solvent-based flavors, and combinations thereof.

Although at least one of the flavor agents present in the effervescent composition includes a flavor integrally associated with a gum Arabic carrier, the flavor agent optionally includes at least one additional integrally associated carrier other than gum Arabic. In addition or alternatively, the composition can optionally include at least one other flavor agent that includes a flavor and a carrier other than gum Arabic. Examples of other suitable carriers include, e.g., sucrose, dextrose, lactose, fructose, maltose, ribose, dextrose, arabinose, pentose, xylose, galactose, and isomalt (e.g., a mixture of glucopyranosylmannitol dihydrate and glucopyranosylsorbitol), and combinations thereof, sugar alcohols (e.g., sorbitol, mannitol, xylitol, lactitol, maltitol, and pentatol, and combinations thereof), casein, starches (e.g., natural and modified starches (e.g., octenyl succinate starch)), hydrolyzed starches (e.g., maltodextrin), dextrin (e.g., water soluble and partially water soluble dextrins), cyclodextrin, and emulsifying polymers, pectins, xanthans, alginates, hydrocolloids, cellulose (e.g., carboxymethyl cellulose, methyl cellulose, ethyl cellulose, hydroxyethylcellulose, and hydroxypropyl cellulose), corn syrup (e.g., corn syrup solids), silicon dioxide, soy lecithin, modified starch (e.g., sodium starch octenyl succinates), proteins (e.g., whey protein), monosaccharides, disaccharides, trisaccharides, gelatin, agar, alginate, carrageenan, tragacanth, butylated hydroxyanisole, butylated hydroxytoluene, and combinations thereof.

The integral association of the flavor and the carrier can exist in a variety of forms including, e.g., flavor fully or partially encapsulated by the carrier, flavor plated on the carrier, flavor in a uniform mixture with the carrier, and combinations thereof. The flavor and carrier become integrally associated with one another as a result of the process of making the flavor agent. Such processes include, e.g., plating, encapsulation (e.g., coacervation and complex coacervation techniques), emulsification, mixing, spray drying, granulating, agglomeration, extrusion, and combinations thereof.

A number of suitable flavor agents are commercially available including, e.g., PRINOVA flavors from Prinova Group LLC. (Carol Stream, Ill.), SIMPLY NATURAL flavors from Edgar Weber & Co. (Wheeling, Ill.), FONA flavors from Fona International Inc. (Geneva, Ill.), Symrise Inc. (Teterboro, N.J.), and from DRIZOOM flavors from Zoomessence (Hebron, Ky.).

The flavor agent can be present in the effervescent composition in any suitable amount. The effervescent composition preferably includes at least 0.1% by weight, at least 1% by weight, at least 1.5% by weight, at least 2% by weight, less than 6% by weight, less than 5% by weight, from 1% by weight to 6% by weight, from 1.5% by weight to 6% by weight, or even from 2% by weight to 5% by weight of a flavor agent that includes gum Arabic.

The effervescent composition optionally is free of a flavor agent that does not include gum Arabic (i.e., free of a flavor agent that is free of gum Arabic).

The effervescent composition also optionally includes oil (e.g., botanical oil, mineral oil, synthetic oil, or a combination thereof). Useful botanical oils include, e.g., avocado oil, wheat germ oil, coconut oil, an oil, safflower oil, sesame oil, sunflower oil, flax seed oil, canola oil, cotton seed oil, corn oil, palm oil, olive oil, and combinations thereof. The effervescent composition preferably includes less than 2% by weight, less than 1% by weight, less than 0.8% by weight, at least 0.1% by weight, at least 0.2% by weight, at least 0.3% by weight, at least 0.4% by weight, at least 0.5% by weight, at least 0.6% by weight, from 0.3% by weight to 1% by weight, from 0.3% by weight to 0.8% by weight, or even from 0.5% by weight to 0.8% by weight oil.

The effervescent composition optionally includes a lubricant derived from rice hulls. The lubricant preferably is in the form of a free-flowing powder that includes rice hull particles, which can be produced by any suitable process including, e.g., grinding rice hulls, crushing rice hulls, and combinations thereof. Useful lubricants include multi-component integral lubricants that include rice hull particles and a variety of components combined in the form of a single substance. Suitable components for the multi-component integral lubricant include, e.g., extracts of rice (e.g., lipids, proteins, complex carbohydrates, and combinations thereof), rice hull particles, gum Arabic, silica derived from rice (e.g., free flowing silica powder derived from rice), oil (e.g., sunflower oil, avocado oil, and combinations thereof), polysaccharide (e.g., starch, amylopectin, and combinations thereof), and combinations thereof. One particularly useful example of a multi-component integral lubricant is commercially available under the NUMAG trade designation from Ribus Inc. (St. Louis, Mo.) and includes an integral mixture of extracts of rice, ground rice hulls, gum Arabic and sunflower oil.

The effervescent composition preferably includes at least 0.1% by weight, at least 0.2% by weight, at least 0.5% by weight, no greater than 5% by weight, no greater than 4% by weight, from 0.5% by weight to 4% by weight, from 0.8% by weight to 4% by weight, from 0.8% by weight to 2% by weight, or even from 0.8% by weight to 1.5% by weight of a lubricant derived from rice hulls.

The effervescent composition optionally includes additional ingredients including, e.g., lubricants other than those derived from rice hulls, binders other than crystalline sugar binders, color agents, nutritional ingredients (e.g., nutritional supplements), surfactant, and combinations thereof.

The oils mentioned above can provide a lubricant function by enabling the effervescent composition to be tableted without sticking to the tablet press or creating other tableting problems. The composition can optionally include a variety of other lubricants including, e.g., water insoluble, water dispersible, and water soluble lubricants, and combinations thereof. Examples of useful water soluble lubricants include sodium benzoate, polyethylene glycol, L-leucine, adipic acid, and combinations thereof. Water insoluble lubricants include, e.g., animal fats, polyoxyethylene monostearate, talc, and combinations thereof. When lubricant is present in the effervescent composition, it preferably is present in less than 2% by weight, less than 1% by weight, less than 0.8% by weight, from 0.05% by weight to 1% by weight, or even from 0.05% by weight to 0.8% by weight.

Other binders that can optionally be present as a secondary or additional binder in the composition include, e.g., amorphous binders, agglomerated dextrose, starches, natural gums, cellulose gums, microcrystalline cellulose, methylcellulose, cellulose ethers, sodium carboxymethylcellulose, ethyl cellulose, gelatin, sorbitol, mannitol, polyethylene glycol, polyvinylpyrrolidone, pectins, alginates, polyacrylamides, polyvinyloxoazolidone, polyvinylalcohols, multicomponent integral binders, and mixtures thereof. Examples of other binders that are not the crystalline sugar binders referred to above include sucrose-based binders commercially available under the DI-PAC trade designation from Le Melange LLC, (Lake Worth, Fla.) and the compressible dextrose-based binders commercially available under the CANTAB trade designation from Stauber (Fullerton, Calif.).

Useful color agents include, e.g., food, drug and cosmetic (FD&C) colors including, e.g., dyes, pigments, lakes, natural colorants, and derived colorants. Useful naturally derived color agents include color agents derived from beet root, yellow beet root, riboflavin, spirulina, vegetable juice color agent, and combinations thereof. Useful lakes include dyes absorbed on aluminum hydroxide and other suitable carriers. Examples of suitable colors include FD&C Red No. 3, FD&C Red No. 40, FD&C Blue No. 1, FD&C Blue No. 2, FD&C Yellow No. 5, FD&C Yellow No. 6, FD&C Green No. 3, and combinations thereof.

The color agent optionally includes a carrier integrally associated with the coloring component such that the color component is fully or partially encapsulated by the carrier, plated on the carrier, in a uniform mixture with the carrier, or a combination thereof. Useful carriers include, e.g., sucrose, dextrose, lactose, fructose, maltose, ribose, arabinose, pentose, xylose, galactose, and isomalt (e.g., a mixture of glucopyranosylmannitol dihydrate and glucopyranosylsorbitol), and combinations thereof, and sugar alcohols including, e.g., sorbitol, mannitol, xylitol, lactitol, maltitol, and pentatol, and combinations thereof. Other carriers include, e.g., starch, modified starch, hydrolyzed starches (e.g., maltodextrin), dextrin (e.g., water soluble and partially water soluble dextrins), and emulsifying polymers (e.g., gum arabic), pectins, xanthans, alginates, cellulose (e.g., carboxymethyl cellulose, methyl cellulose, ethyl cellulose, hydroxyethylcellulose, and hydroxypropyl cellulose), corn syrup (e.g., corn syrup solids), silicon dioxide, soy lecithin, butylated hydroxyanisole, butylated hydroxytoluene, and combinations thereof. Starch is an example of a water insoluble carrier.

The effervescent composition can include any suitable amount of the optional color agent including, e.g., less than 3% by weight, less than 2% by weight, less than 1% by weight, less than 0.5% by weight, at least 0.05% by weight, or even from 0.1% by weight to 0.5% by weight color agent.

Active agents that are optionally present in the effervescent composition include, e.g., medicaments, vitamins, minerals, amino acids, other dietary supplements, herbs, and combinations thereof. Examples of useful vitamins include, e.g., ascorbic acid (vitamin C), aspartic acid, thiamin, riboflavin, nicotinic acid, pantothenic acid, pyridoxine, biotin, folic acid, niacin, vitamin B12, lipoic acid, vitamin A, vitamin D, vitamin E and vitamin K and coenzymes thereof, choline, carnitine, and alpha, beta, and gamma carotenes.

Examples of coenzymes include thiamine pyrophosphates, flavin mononucleotide, flavin adenine dinucleotide, nicotinamide adenine dinucleotide, nicotinamide adenine dinucleotide phosphate coenzyme A pyridoxal phosphate, biocytin, tetrahydrofolic acid, coenzyme B12, lipoyllysine, 11-cis-retinal, and 1,25-dihydroxycholecalciferol, and mixtures thereof.

Examples of useful minerals include iron, zinc, calcium, sodium, potassium, manganese, selenium, copper, iodine, magnesium, phosphorus, and chromium and combinations thereof.

Useful amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and combinations thereof. Other dietary supplements include, e.g., bee pollen, bran, wheat germ, kelp, cod liver oil, ginseng, fish oils, proteins, and combinations thereof.

Useful herbs and extracts of herbs include, e.g., ginger, sage, thyme, red clover, black cohosh, and combinations thereof, *ginseng, Echinacea,* elderberry extract, and extracts thereof.

The ingredients of the effervescent composition can be sieved as necessary prior to combining with mixing.

The effervescent composition can be formed into tablets of any useful size and dimension including, e.g., tablets having a diameter of at least 10 mm, at least 15 mm, at least 20 mm, from 15 mm to 30 mm, from 20 mm to 30 mm, or even 25 mm, and a weight of at least 1 g, at least 3 g, at least 4 g, from 1 g to 7 g, from 2 g to 6.5 g, from 3 g to 6 g, or even from 4 g to 6 g.

The effervescent composition is well-suited to the mass production of effervescent tablets. The effervescent composition preferably can be tableted on a high speed tableting press to form tablets. Any suitable tablet mass production equipment and processes can be used. Examples of useful tableting processes for effervescent compositions are described in Pharmaceutical Dosage Forms, Vol. 1, (Herbert A. Lieberman et al. eds, $2^{nd}$ ed. 1989) and incorporated herein. The tablets can then be manufactured in an automated process in which multiple dies of a tablet press are filled sequentially or simultaneously with the effervescent composition, two punches compress the effervescent composition to form the tablet(s), and then the tablet(s) is ejected from the die. The dies optionally include a lubricant.

The tablet is then placed in packaging material, which is then sealed to form an air tight sealed package. The packaged tablet can be further processed by conveying it to other processing stations including, e.g., additional packaging stations for further packaging, e.g., boxing and bagging.

The tablet manufacturing and initial packing operations are preferably performed in a controlled environment in which the temperature and humidity are controlled. Preferably the controlled environment has less than 18 grains, less than 16 grains, or even less than 15 grains of moisture per pound of air at a temperature of 72° F. (22.2° C.).

The effervescent tablets are preferably stored in a moisture-proof package. Useful moisture proof packages are in a variety of forms, including, e.g., sealed metal foil pouches, blister packs, and desiccant capped tubes. Useful packaging materials also include, e.g., plastic, metal foil, plastic films, capped tubes, and blister packaging.

A useful method of using the effervescent tablets includes dissolving a tablet in excess water, e.g., an eight-ounce, twelve-ounce or sixteen-ounce glass of water, a bottle of water and combinations thereof, to form an aqueous solution, and then ingesting the resulting composition. After addition of the effervescent composition to an aqueous liquid, the composition optionally can be stirred to further facilitate disintegration in the aqueous liquid.

The invention will now be described by way of the following examples. All parts, ratios, percentages and amounts stated in the Examples are by weight unless otherwise specified.

EXAMPLES

Test Procedures

Test procedures used in the examples are set forth below. All ratios and percentages are by weight unless otherwise indicated. The procedures are conducted at room temperature (i.e., an ambient temperature of from 20° C. to 25° C.) unless otherwise specified.

Hardness Test Method

The hardness of the tablets is measured using a Dr. Schleuniger Pharmatron hardness tester according to USP <1217> Tablet Breaking Force test method.

Disintegration Time Test Method

A timer is started simultaneously with adding one tablet to 500 mL of 25° C.+/−2° C. water and is stopped either when the tablet is fully disintegrated or no tablet pieces having a dimension of at least 0.25 inches (0.635 cm) are present. The time reflected on the timer is recorded in units of seconds.

% Moisture Test Method

The percent moisture present in a crystalline sugar binder is determined using a standardized Karl Fischer Moisture Analyzer according to USP 2018 Water Determination test method <921> 1a.

Base 1

Base 1 was prepared by combining, with mixing, 52.09% by weight sodium bicarbonate No. 5, 16.35% by weight sodium carbonate, 19.15% by weight potassium carbonate, 6.10% by weight potassium chloride, 3.53% by weight magnesium oxide, and 2.78% by weight calcium carbonate.

Base 2

Base 1 was prepared by combining, with mixing, 28.84% by weight sodium bicarbonate No. 5, 36.22% by weight sodium carbonate, 21.20% by weight potassium carbonate, 6.76% by weight potassium chloride, 3.91% by weight magnesium oxide, and 3.07% by weight calcium carbonate.

Examples E1-E11 and Controls C1-C22

The effervescent compositions of Examples E1-E11 and Controls C1-C22 were prepared by combining, with mixing, citric acid fine granular and then each of the ingredients set forth in Table 1, with the exception of the Avocado oil, in a Kitchen Aid mixer. The order of addition was from the ingredient present in the composition in the smallest amount to the largest amount. The amount of each ingredient set forth in Tables 1 and 2 is in units of % by weight based on the total weight of the formulation. When necessary, an ingredient was sieved using a number 12 sieve prior to addition to the mixture. After mixing the composition for ten minutes, the oil was added over a period of five minutes with mixing. The resulting compositions were then screened through a six mesh sieve.

The compositions were then tableted on a Cadmach rotary compression machine using 1 inch diameter stainless steel tools with a bisect. The average weight (in grams), thickness (in inches), and hardness (in kiloponds) of ten tablets was measured and is reported in Tables 1 and 2. The tablets were then tested according to the Disintegration Time Test Method and the average tablet disintegration time is reported in Table 1 in units of minutes and seconds (min: sec).

TABLE 1

|  | C1 | C2 | E1 | E2 | C3 | C4 | E3 | E4 |
|---|---|---|---|---|---|---|---|---|
| CANTAB Dextrose[1] | 29.79 | 29.51 | 0.00 | 0.00 | 29.79 | 29.51 | 0.00 | 0.00 |
| ADM Dextrose[2] | 0.00 | 0.00 | 29.79 | 29.51 | 0.00 | 0.00 | 29.79 | 29.51 |
| Citric Acid, Fine Granular | 35.86 | 35.52 | 35.86 | 35.52 | 35.86 | 35.52 | 35.86 | 35.52 |
| Citrus Orange Flavor[3] | 2.11 | 2.09 | 2.11 | 2.09 | 0.00 | 0.00 | 0.00 | 0.00 |
| Orange Flavor[4] | 1.91 | 1.89 | 1.91 | 1.89 | 1.91 | 1.89 | 1.91 | 1.89 |
| Citrus Orange Flavor[5] | 0.00 | 0.00 | 0.00 | 0.00 | 2.11 | 2.09 | 2.11 | 2.09 |
| Malic Acid | 1.84 | 1.82 | 1.84 | 1.82 | 1.84 | 1.82 | 1.84 | 1.82 |
| Stevia 95% | 0.51 | 0.51 | 0.51 | 0.51 | 0.51 | 0.51 | 0.51 | 0.51 |
| AvocadoOil | 0.51 | 0.50 | 0.51 | 0.50 | 0.51 | 0.50 | 0.51 | 0.50 |
| NuMag[6] Natural | 0.00 | 0.95 | 0.00 | 0.95 | 0.00 | 0.95 | 0.00 | 0.95 |
| Base #1 | 27.46 | 27.20 | 27.46 | 27.20 | 27.46 | 27.20 | 27.46 | 27.20 |
| Weight (g) | 5.44 | 5.49 | 5.43 | 5.49 | 5.44 | 5.49 | 5.44 | 5.49 |
| Thickness (in) | 0.296 | 0.293 | 0.29 | 0.297 | 0.296 | 0.294 | 0.292 | 0.296 |
| Hardness (kp) | 9.3 | 8.4 | 10.2 | 4.9 | 9.3 | 8.2 | 9.9 | 5.2 |
| Disintegration Time (min:sec) | 4:04 | 3:56 | 3:15 | 2:06 | 3:59 | 3:43 | 3:04 | 1:51 |

[1]= CANTAB compressible dextrose (Stauber Performance Ingredients, Inc., Fullerton, California)
[2]= Crystalline dextrose no less than 99.5% dextrose (Archer Daniels Midland Company, Chicago, Illinois)
[3]= Citrus Orange Flavor 188-65-C including maltodextrin, modified food starch and natural flavors (Edgar A. Weber & Co., Wheeling, Illinois)
[4]= NGP N-C Orange WONF Flavor 884.2186 U greater than 50% by weight gum Arabic, from 25% by weight to 50% by weight natural flavor, from 2% by weight to 5% by weight medium chain triglycerides, and less than 2% by weight DL-alpha tocopherol (Fona International, Geneva, Illinois)
[5]= 28-17-0224SD Citrus Orange Flavor MWNI SD from 89% by weight to 93% by weight gum Arabic and from 7% by weight to 11% by weight natural flavor (Edgar A. Weber & Co., Wheeling, Illinois)
[6]= Nu-MAG certified organic fine powder (Ribus, Inc., St. Louis, Missouri)

TABLE 2

|  | C5 | C6 | C7 | C8 | C9 | C10 | E5 | E6 |
|---|---|---|---|---|---|---|---|---|
| CANTAB Dextrose | 30.05 | 29.74 | 0.00 | 0.00 | 30.05 | 29.74 | 0.00 | 0.00 |
| ADM Dextrose | 0.00 | 0.00 | 30.05 | 29.74 | 0.00 | 0.00 | 30.05 | 29.74 |
| Citric Acid, Fine Granular | 40.80 | 40.39 | 40.80 | 40.39 | 40.80 | 40.39 | 40.80 | 40.39 |
| Natural TriBerry Flavor[7] | 2.32 | 2.30 | 2.32 | 2.30 | 0.00 | 0.00 | 0.00 | 0.00 |
| Natural TriBerry Flavor[8] | 0.00 | 0.00 | 0.00 | 0.00 | 2.32 | 2.30 | 2.32 | 2.30 |
| Malic Acid | 0.74 | 0.73 | 0.74 | 0.73 | 0.74 | 0.73 | 0.74 | 0.73 |
| Stevia 95% | 0.56 | 0.55 | 0.56 | 0.55 | 0.56 | 0.55 | 0.56 | 0.55 |
| Avocado Oil | 0.52 | 0.51 | 0.52 | 0.51 | 0.52 | 0.51 | 0.52 | 0.51 |
| NuMag Natural | 0 | 1.01 | 0 | 1.01 | 0 | 1.01 | 0 | 1.01 |
| Base #2 | 25.01 | 24.76 | 25.01 | 24.76 | 25.01 | 24.76 | 25.01 | 24.76 |
| Weight (g) | 5.39 | 5.45 | 5.39 | 5.44 | 5.39 | 5.45 | 5.39 | 5.44 |
| Thickness (in) | 0.3 | 0.293 | 0.299 | 0.295 | 0.301 | 0.295 | 0.3 | 0.296 |
| Hardness (kp) | 9 | 9.4 | 10.1 | 5.7 | 9.2 | 9.5 | 10.7 | 6.8 |
| Disintegration Time (min:sec) | 10:19 | 9:38 | 9:03 | 6:55 | 4:09 | 3:39 | 3:24 | 2:29 |

[7]= Natural tri-berry-type flavor 31672 including modified corn starch, natural flavor and tocopherol (Prinova Group LLC, Carol Stream, Illinois)
[8]= Natural tri-berry-type flavor 23339 including from 45% by weight to 55% by weight gum Arabic, from 30% by weight to 40% by weight maltodextrin, and from 10% by weight to 20% by weight natural flavor (Prinova Group LLC, Carol Stream, Illinois)

TABLE 3

|  | C11 | C12 | C13 | C14 | C15 | C16 | E8 | E9 |
|---|---|---|---|---|---|---|---|---|
| CANTAB Dextrose | 29.38 | 29.08 | 0.00 | 0.00 | 29.38 | 29.08 | 0.00 | 0.00 |
| ADM Dextrose | 0.00 | 0.00 | 29.38 | 29.08 | 0.00 | 0.00 | 29.38 | 29.08 |
| Citric Acid, Fine Granular | 40.39 | 39.99 | 40.39 | 39.99 | 40.39 | 39.99 | 40.39 | 39.99 |
| Strawberry Lemonade Flavor[9] | 1.65 | 1.64 | 1.65 | 1.64 | 0.00 | 0.00 | 0.00 | 0.00 |
| Natural Strawberry Lemonade Flavor[10] | 0.00 | 0.00 | 0.00 | 0.00 | 1.65 | 1.64 | 1.65 | 1.64 |
| Stevia 95% | 0.66 | 0.65 | 0.66 | 0.65 | 0.66 | 0.65 | 0.66 | 0.65 |
| Avocado Oil | 0.50 | 0.50 | 0.50 | 0.50 | 0.50 | 0.50 | 0.50 | 0.50 |
| NuMag Natural | 0.00 | 1.00 | 0.00 | 1.00 | 0.00 | 1.00 | 0.00 | 1.00 |
| Base #1 | 27.41 | 27.14 | 27.41 | 27.14 | 27.41 | 27.14 | 27.41 | 27.14 |
| Weight (g) | 5.45 | 5.5 | 5.45 | 5.5 | 5.45 | 5.5 | 5.45 | 5.51 |
| Thickness (in) | 0.3 | 0.296 | 0.294 | 0.294 | 0.296 | 0.294 | 0.294 | 0.294 |
| Hardness (kp) | 8.8 | 8.5 | 10.4 | 5.8 | 8.9 | 7.6 | 9.7 | 5.7 |
| Disintegration Time (min:sec) | 8:21 | 7:51 | 7:24 | 6:00 | 4:21 | 3:29 | 3:49 | 2:26 |

[9]= 193-17-A Strawberry Lemonade Flavor 68% by weight modified food starch (waxy maize), 9% by weight maltodextrin, 5% by weight citric acid, and natural flavors (Edgar A. Weber & Co., Wheeling, Illinois)
[10]= 28-18-0118SD Strawberry Lemonade Flavor MWNI SD from 71% by weight to 81% by weight gum Arabic, 15% by weight to 25% by weight, and from 1% by weight to 5% byweight (Edgar A. Weber & Co., Wheeling, Illinois)

Table 4

|  | C17 | C18 | C19 | C20 | C21 | C22 | E10 | E11 |
|---|---|---|---|---|---|---|---|---|
| CANTAB Dextrose | 28.02 | 27.77 |  | 0.00 | 28.02 | 27.77 | 0.00 |  |
| ADM Dextrose | 0.00 | 0.00 | 28.02 | 27.77 | 0.00 | 0.00 | 28.02 | 27.77 |
| Citric Acid, Fine Granular | 39.78 | 39.42 | 39.78 | 39.42 | 39.78 | 39.42 | 39.78 | 39.42 |
| Orange Flavor[11] | 2.42 | 2.40 | 2.42 | 2.40 | 0.00 | 0.00 | 0.00 | 0.00 |
| Natural Orange Flavor[12] | 0.00 | 0.00 | 0.00 | 0.00 | 2.42 | 2.40 | 2.42 | 2.40 |
| Malic Acid | 0.26 | 0.26 | 0.26 | 0.26 | 0.26 | 0.26 | 0.26 | 0.26 |
| Stevia 95% | 0.52 | 0.51 | 0.52 | 0.51 | 0.52 | 0.51 | 0.52 | 0.51 |
| Avocado Oil | 0.48 | 0.48 | 0.48 | 0.48 | 0.48 | 0.48 | 0.48 | 0.48 |
| NuMag Natural | 0.00 | 0.91 | 0.00 | 0.91 | 0.00 | 0.91 | 0.00 | 0.91 |
| Base 2 | 28.51 | 28.25 | 28.51 | 28.25 | 28.51 | 28.25 | 28.51 | 28.25 |
| Weight (g) | 5.78 | 5.83 | 5.78 | 5.83 | 5.78 | 5.83 | 5.78 | 5.84 |
| Thickness (in) | 0.315 | 0.31 | 0.316 | 0.313 | 0.307 | 0.312 | 0.315 | 0.313 |
| Hardness (kp) | 9.9 | 9.6 | 9.4 | 6.7 | 9.6 | 8.4 | 9.9 | 6.5 |
| Disintegration Time (min:sec) | 7:07 | 6:44 | 6:05 | 4:41 | 4:48 | 4:08 | 3:50 | 2:38 |

[11]= Natural Orange Flavor WONF 16936 from 40% by weight to 50% by weight modified corn starch, from 40% by weight to 50% by weight maltodextrin, 10% by weight to 20% by weight natural flavors (Prinova Group LLC, Carol Stream, Illinois)
[12]= Natural Orange Flavor 23338 gumArabic and natural flavor (Prinova Group LLC)

Other embodiments are within the claims. Documents referred to herein are hereby incorporated.

1. An effervescent tablet comprising: an effervescent agent comprising an acid and a base; a sweetener comprising Stevia, Monk fruit, or a combination thereof; a first crystalline sugar binder selected from the group consisting of crystalline dextrose, crystalline sucrose, crystalline fructose, and combinations thereof, the crystalline sugar binder being essentially free of excipients; and a flavor agent comprising gum Arabic, the effervescent tablet having a weight of at least 4 grams and a hardness of at least 5 kiloponds and exhibiting a disintegration time of no greater than 4 minutes and 20 seconds when tested according to the Disintegration Time Test Method.

2. The effervescent tablet of paragraph 1, wherein the crystalline sugar binder comprises crystalline dextrose monohydrate.

3. The effervescent tablet of paragraph 1, wherein the crystalline sugar binder comprises crystalline dextrose monohydrate and crystalline fructose.

4. The effervescent tablet of any one of paragraphs 1-3, wherein the effervescent tablet dissintegrates in 25° C. water in no greater than 3.5 minutes, or even no greater than 120 seconds.

5. The effervescent tablet of any one of paragraphs 1-4 comprising at least 20% by weight of the effervescent agent; and from 20% by weight to 55% by weight of the crystalline sugar binder.

6. The effervescent tablet of any one of paragraphs 1-5 comprising from 0.4% by weight to 2% by weight of the sweetener.

7. The effervescent tablet of paragraph 2 comprising at least 20% by weight of the effervescent agent; and from 20% by weight to 55% by weight of the crystalline sugar binder.

8. The effervescent tablet of paragraph 7 comprising from 0.4% by weight to 2% by weight of the sweetener.

9. The effervescent tablet of any one of paragraphs 1-8 further comprising oil.

10. The effervescent tablet of any one of paragraphs 1-8 further comprising avocado oil.

11. The effervescent tablet of any one of paragraphs 1-10 further comprising at least 0.50% by weight oil.

12. The effervescent tablet of any one of paragraphs 1-11 having a hardness of at least 6 kiloponds, or even a hardness of at least 7 kiloponds.

13. The effervescent tablet of any one of paragraphs 1-12, comprising at least 1.5% by weight of a flavor agent that comprises gum Arabic.

14. The effervescent tablet of any one of paragraphs 1-12, comprising at least 2% by weight of a flavor agent that comprises gum Arabic.

15. The effervescent tablet of any one of paragraphs 1-2, wherein the tablet is free of flavor agents that are free of gum Arabic.

16. The effervescent tablet of any one of paragraphs 1-15 further comprising a lubricant derived from rice hull, a lubricant comprising rice hull particles, or a combination thereof.

17. The effervescent tablet of any one of paragraphs 1-15 further comprising a multi-component integral lubricant comprising rice hull particles, gum Arabic, sunflower oil and at least one extract of rice.

18. A method of making an effervescent tablet, the method comprising: forming an effervescent composition by combining ingredients with mixing, the ingredients comprising an effervescent agent comprising an acid and a base, a sweetener comprising Stevia, Monk fruit, or a combination thereof, a first crystalline sugar binder selected from the group consisting of crystalline dextrose, crystalline sucrose, crystalline fructose, and combinations thereof, the crystalline sugar binder being essentially free of excipients, and a flavor agent comprising gum Arabic; and tableting the effervescent composition on a tableting press to form an effervescent tablet that has a mass of at least 4 grams and a hardness of at least 5 kiloponds (kp) and that disintegrates in 25° C. water in less than 5 minutes.

19. The method of paragraph 18, wherein the crystalline sugar binder comprises at least 6% moisture.

20. The method of any one of paragraphs 18 and 19, wherein the crystalline sugar binder is free of excipients.

21. The method of any one of paragraphs 18-20, wherein the crystalline sugar binder exhibits an average particle size of from 140 μm to 440 μm.

22. The method of any one of paragraphs 18-21, wherein the crystalline sugar binder comprises crystalline dextrose monohydrate.

23. The method of any one of paragraphs 18-21, wherein the crystalline sugar binder comprises crystalline dextrose and crystalline fructose.

24. The method of any one of paragraphs 18-21, wherein the crystalline sugar binder comprises crystalline dextrose monohydrate and crystalline fructose.

25. The method of any one of paragraphs 18-24, wherein the effervescent tablet has a hardness of at least 6 kp, or even at least 7 kp.

26. The method of any one of paragraphs 18-25, wherein the ingredients further comprise a lubricant derived from rice hulls.

27. The method of any one of paragraphs 18-25, wherein the ingredients further comprise a multi-component integral lubricant comprising rice hull particles, gum Arabic, sunflower oil, and at least one extract of rice.

28. The method of any one of paragraphs 18-27, or the effervescent tablet of any one of paragraphs 1-17, further comprising from 0.8% by weight to 4% by weight of a lubricant derived from rice hulls.

29. The method of any one of paragraphs 18-27, or the effervescent tablet of any one of paragraphs 1-17, further comprising from 0.8% by weight to 1.5% by weight of a lubricant derived from rice hulls.

What is claimed is:

1. An effervescent tablet comprising:
   at least 20% by weight of an effervescent agent comprising an acid and a base;
   a sweetener comprising Stevia, Monk fruit, or a combination thereof;
   from 20% by weight to 55% by weight of a first sugar binder selected from the group consisting of unagglomerated dextrose crystals, unagglomerated sucrose crystals, unagglomerated fructose crystals, and combinations thereof, the sugar binder being essentially free of excipients; and
   least 1.5% by weight of a flavor agent comprising gum Arabic,
   the effervescent tablet having a weight of at least 4 grams and a hardness of at least 5 kiloponds and exhibiting a disintegration time of no greater than 4 minutes and 20 seconds when tested according to the Disintegration Time Test Method.

2. The effervescent tablet of claim 1, wherein the sugar binder comprises unagglomerated dextrose monohydrate crystals.

3. The effervescent tablet of claim 1, wherein the sugar binder comprises unagglomerated dextrose monohydrate crystals and unagglomerated fructose crystals.

4. The effervescent tablet of claim 1, wherein the tablet disintegrates in 25° C. water in no greater than 3.5 minutes.

5. The effervescent tablet of claim 1 comprising from 0.4% by weight to 2% by weight of the sweetener.

6. The effervescent tablet of claim 2 comprising
   from 20% by weight to 55% by weight of the unagglomerated dextrose monohydrate crystals sugar binder.

7. The effervescent tablet of claim 6 comprising from 0.4% by weight to 2% by weight of the sweetener.

8. The effervescent tablet of claim 1 further comprising oil.

9. The effervescent tablet of claim 1 further comprising avocado oil.

10. The effervescent tablet of claim 1 further comprising at least 0.50% by weight oil.

11. The effervescent tablet of claim 1 having a hardness of at least 6 kiloponds.

12. The effervescent tablet of claim 1, comprising at least 2% by weight of the flavor agent that comprises gum Arabic.

13. The effervescent tablet of claim 1, wherein the tablet is free of flavor agents that are free of gum Arabic.

14. The effervescent tablet of claim 2 further comprising a lubricant derived from rice hulls.

15. The effervescent tablet of claim 1 further comprising a multi-component integral lubricant comprising rice hull particles, gum Arabic, sunflower oil and at least one extract of rice.

16. The effervescent tablet of claim 1 further comprising a lubricant derived from rice hulls.

* * * * *